United States Patent
Day et al.

(10) Patent No.: US 8,338,736 B2
(45) Date of Patent: Dec. 25, 2012

(54) EXTRACTION OF CHORDAL TEST SPECIMENS FROM FORGINGS

(75) Inventors: Christophe Jude Day, Beverly, MA (US); Mark Douglas Ehresman, Haverhill, MA (US); Clifford Edward Allen, Jr., Newbury, MA (US); Mark Joseph Gleason, Madisonville, KY (US); Michael Joseph Gambone, Mason, OH (US)

(73) Assignee: General Electric Company, Schenectady, NY (US)

( * ) Notice: Subject to any disclaimer, the term of this patent is extended or adjusted under 35 U.S.C. 154(b) by 1161 days.

(21) Appl. No.: 12/196,026

(22) Filed: Aug. 21, 2008

(65) Prior Publication Data

US 2010/0043517 A1 Feb. 25, 2010

(51) Int. Cl.
*B23H 9/00* (2006.01)
*B23H 7/02* (2006.01)
(52) U.S. Cl. .......................... 219/69.17; 83/54
(58) Field of Classification Search ............... 219/69.12, 219/69.17; 83/54; 408/1 R, 204, 207
See application file for complete search history.

(56) References Cited

U.S. PATENT DOCUMENTS

| | | | | |
|---|---|---|---|---|
| 4,539,459 A | * | 9/1985 | Yamagata | 219/69.12 |
| 4,544,819 A | * | 10/1985 | Nomura et al. | 219/69.12 |
| 4,547,646 A | * | 10/1985 | Briffod | 219/69.12 |
| 4,725,704 A | * | 2/1988 | Vuichard | 219/69.12 |
| 4,743,729 A | * | 5/1988 | Beal | 219/69.12 |
| 4,796,465 A | * | 1/1989 | Carreno et al. | 73/112.01 |
| 4,841,126 A | | 6/1989 | Graeber | |
| 4,960,971 A | * | 10/1990 | Kawanabe | 219/69.12 |
| 5,106,012 A | | 4/1992 | Hyzak et al. | |
| 5,410,117 A | | 4/1995 | Reynier et al. | |
| 5,824,985 A | * | 10/1998 | Lodetti et al. | 219/69.12 |
| 6,008,461 A | | 12/1999 | Iezawa et al. | |
| 6,127,642 A | * | 10/2000 | Gleason et al. | 219/69.15 |
| 6,568,303 B1 | | 5/2003 | Bentley | |

(Continued)

FOREIGN PATENT DOCUMENTS

DE 19810138 A1 * 9/1998

(Continued)

OTHER PUBLICATIONS

Machine translation of German Patent Document DE 19810138, May 2012.*

(Continued)

*Primary Examiner* — Geoffrey S Evans
(74) *Attorney, Agent, or Firm* — General Electric Company; Sushupta T. Sudarshan; David J. Clement

(57) ABSTRACT

A method for making a test specimen includes machining out a chordal core from an annular forging and machining the specimen symmetrical about a chordal axis of the core. A linear cutting tool such as a wire EDM machine is used for the machining which includes at least a partially cylindrical cutting about the chordal axis with the linear cutting tool. A copper or brass tubular EDM electrode may be used. The chordal core may be machined from fat of the forging. The test specimen may have with a gauge section diameter in a range of 0.1-0.5 inches. The EDM process may include directing jets of machining fluid or dielectric in up and down along a cutting portion of an EDM wire of the EDM machine or performing the EDM process in a tank of machining fluid or dielectric with the annular forging submerged in the fluid or dielectric.

38 Claims, 12 Drawing Sheets

U.S. PATENT DOCUMENTS 6,984,358 B2  1/2006  Spencer
7,065,872 B2  6/2006  Ganesh et al.

FOREIGN PATENT DOCUMENTS

| | | | |
|---|---|---|---|
| FR | 582581 | A | 12/1924 |
| JP | 55060611 | A | 7/1980 |
| JP | 63200746 | U | 12/1988 |
| JP | 01088133 | A | 4/1989 |
| JP | 2006150424 | A | 6/2006 |

OTHER PUBLICATIONS

"Standard Test Methods for Tension Testing of Metallic Materials", ASTM International, Designation: E8-04, American Association State Highway and Transportation Officials Standard, AASHTO No. T68, An American National Standard.

PCT/US2009/051911, Search Report and Written Opinion, Nov. 2, 2009.

* cited by examiner

EXTRACTION OF CHORDAL TEST SPECIMENS FROM FORGINGS

BACKGROUND OF THE INVENTION

1. Field of the Invention

This invention relates to ring forgings and, more particularly, to removing test specimens from the ring forgings.

2. Description of Related Art

Gas turbine engines, as well as many other products, incorporate many annular or cylindrical parts made from forgings or ring forgings. The forgings usually have a near net shape form and are machined to produce the part with final part dimensions and finishes. The forgings and parts are circumscribed about an axis of revolution about which they are usually symmetrical. These parts include rotating portions of rotors including disks or stationary casings and the like, including combustor liners.

Mechanical test specimens are made from the forging for mechanical testing for stress and strain capability as part of quality control of the forging process. The process of making and testing the specimen is a destructive test and so sacrificial forgings or test rings are formed integral with the forging. The test rings are made from wasted forging material that is not incorporated in the forged part. The test ring is cut off or otherwise separated from the forging. Arcuate sections of the test ring are cut from the test ring and machined into round bar test specimens of prescribed dimensions for use in subsequent mechanical testing. Test specimens are typically cylindrical, circumscribed about a specimen axis, and have a reduced section disposed between two grip sections. Test specimens may also be rectangular in cross section.

American National Standard Test Methods for Tension Testing of Metallic Materials have been established for making and using these types of test specimens and are described in American Association State Highway and Transportation Officials Standard AASHTO No. T68. These test methods cover the tension testing of metallic materials in any form at room temperature, specifically, the methods of determination of yield strength, yield point elongation, tensile strength, elongation, and reduction of area.

The test ring portion of the forging is a waste of forging material and adds to the cost of the forging and the process of forging and machining the forging. It is highly desirable to eliminate the test ring in the forging and forging process. In some cases entire forging rings are sacrificed.

SUMMARY OF THE INVENTION

A method for making a test specimen from an annular forging having a forging axis of revolution includes machining out a chordal core from the forging and forming the test specimen from the chordal core with the test specimen being symmetrical about a chordal axis that is colinear with a chord extending through the annular forging. A linear cutting tool may be used for the machining which may include at least a partially cylindrical cutting about the chordal axis with the linear cutting tool. The chordal core may be fully machined from fat of the forging.

One embodiment of the machining includes in sequence, a first linear plunge into the forging, the partially cylindrical cutting, a substantially full cylindrical cutting about the chordal axis, and a second linear plunge out of the forging wherein the first and second linear plunges are angularly spaced apart with respect to the chordal axis.

Alternatively, the machining may further include in sequence, a first linear plunge into the forging, the substantially full cylindrical cutting, and a second linear plunge out of the forging through a kerf formed by the first linear plunge.

Another embodiment of the machining includes electrical discharge machining and the linear cutting tool is a wire electrical discharge machining machine. Alternatively, the electrical discharge machining may use a tubular electrode for the machining which may be made of copper or brass. The test specimen may be formed with a gauge section diameter in a range of 0.1-0.5 inches.

A more particular electrical discharge machining method for making the test specimen includes mounting the annular forging in a headstock of carrier of an EDM machine. The EDM machine has a machine head operable for moving and machining in perpendicular X and Y directions and the carrier is operable to translate in the Y direction perpendicular to a forging axis of revolution of the forging. Then presenting the forging to the machine head by translating the carrier in the Y direction and machining out a chordal core from the forging electrical discharge machining using the machine head moving in the X and Y directions. The chordal core has a linear chordal axis colinear with a chord extending through the annular forging. Forming the test specimen from the chordal core such that the test specimen is symmetrical about the chordal axis.

The electrical discharge machining method may further include directing jets of machining fluid or dielectric in up and down Z directions perpendicular to both the X and Y directions and along a cutting portion of an EDM wire which is parallel to the Z directions. The jets may be directed from upper and lower nozzles of upper and lower wire guides respectively supported by the machining head and the cutting portion of the EDM wire extends between the upper and lower wire guides.

Alternatively, the carrier may be a movable table in a tank of the machining fluid or dielectric and the annular forging is submerged in the machining fluid or dielectric.

BRIEF DESCRIPTION OF THE DRAWINGS

The foregoing aspects and other features of the invention are explained in the following description, taken in connection with the accompanying drawings where.

DETAILED DESCRIPTION OF THE INVENTION

Figure 1:
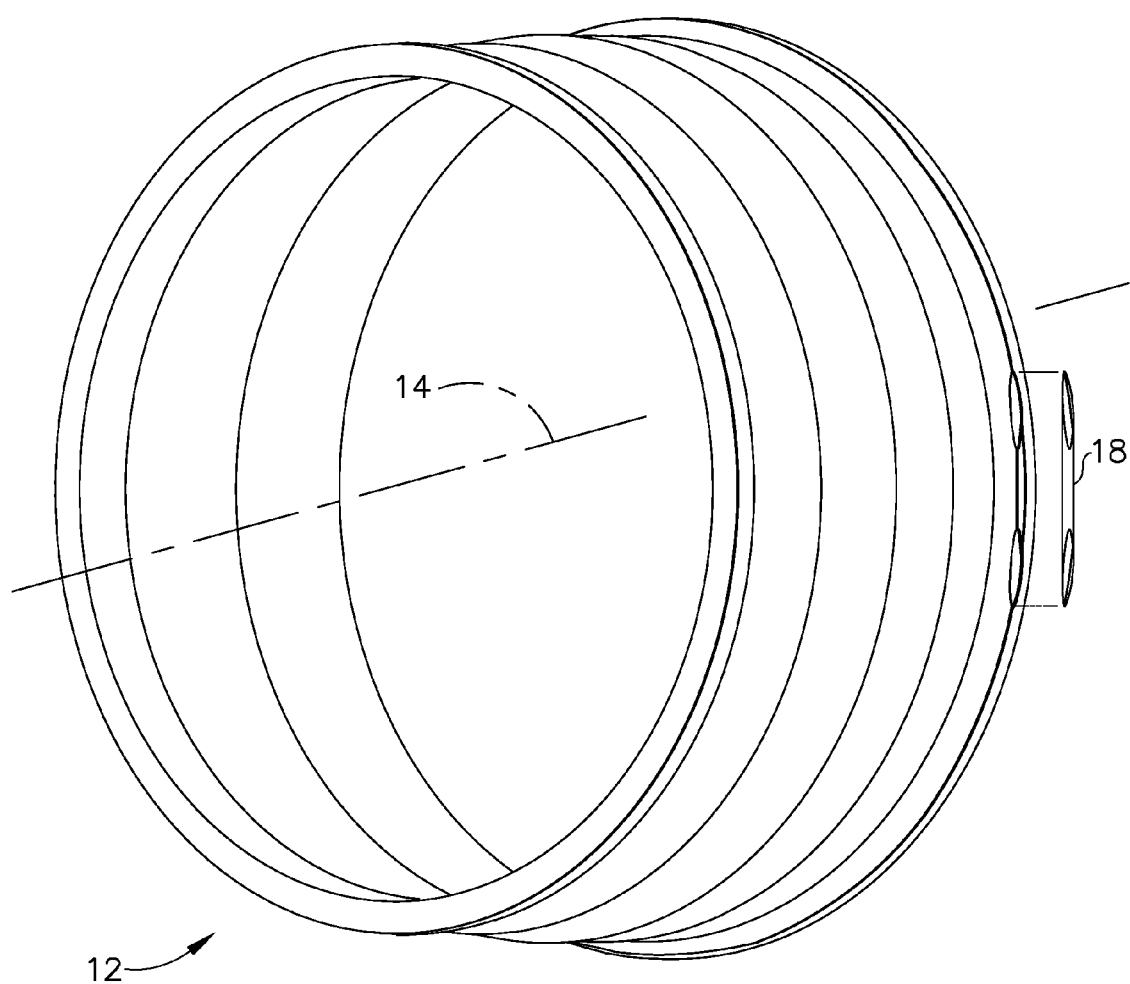
FIG. 1 is a perspective view illustration of an annular gas turbine engine casing casting with a chordal core removed from fat of the forging.
Figure 2:
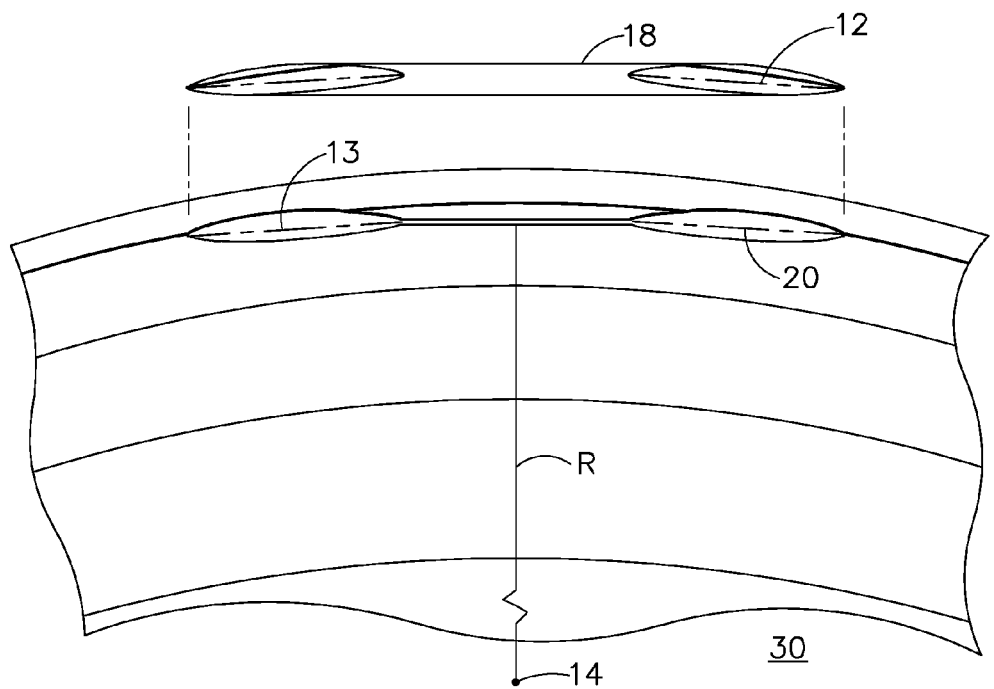
FIG. 2 is an enlarged perspective view illustration of the chordal core removed from the fat of the forging illustrated in FIG. 1.
Figure 4:
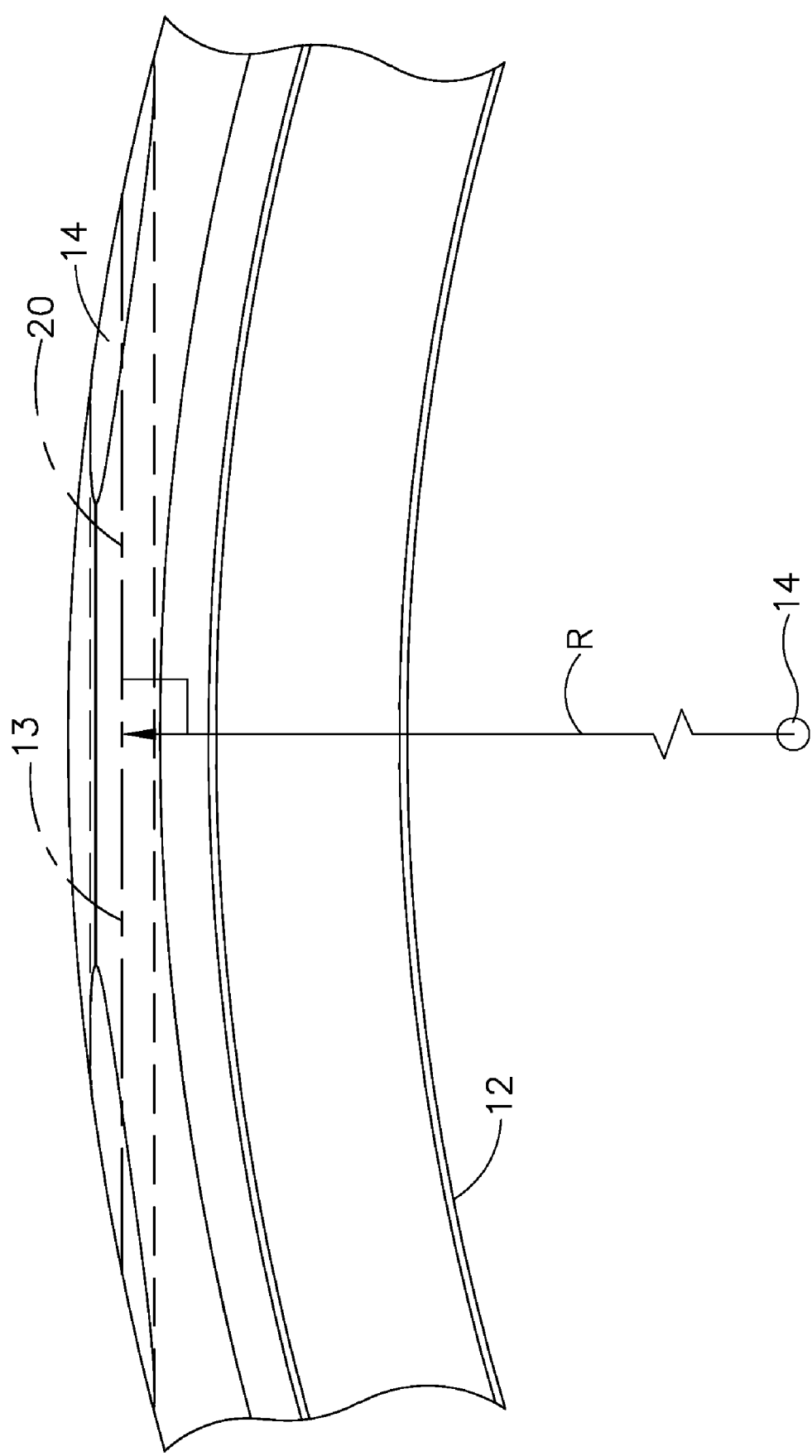
FIG. 4 is an axial cross sectional view illustration of the chordal core in the fat of the forging illustrated in FIG. 3.
Figure 5:
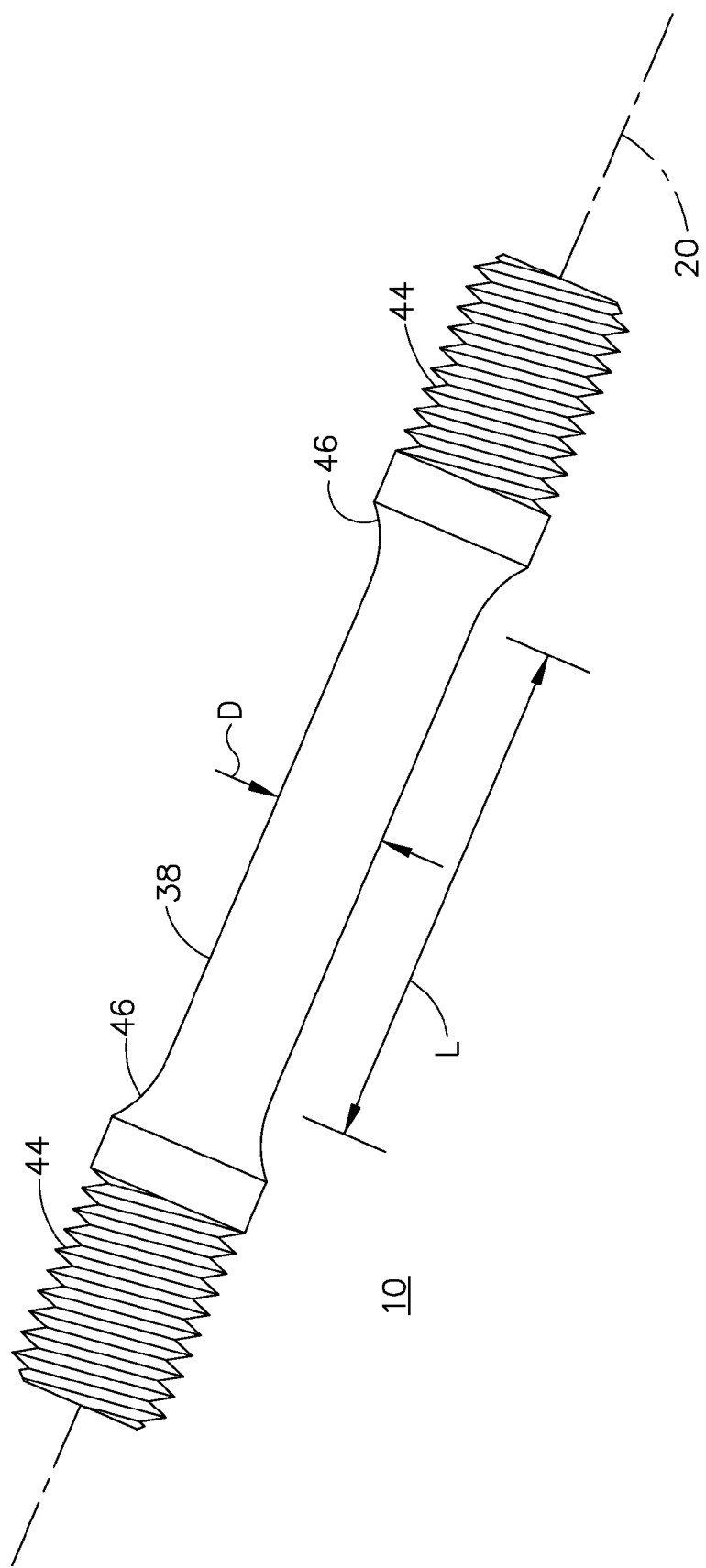
FIG. 5 is a perspective view illustration of a test specimen formed from the chordal core illustrated in FIG. 4.

Illustrated in FIG. 1 is an exemplary method for making a test specimen 10 illustrated in FIG. 5 from an annular forging 12 having a forging axis of revolution 14. The method includes machining 30 out a chordal core 18 from the annular forging 12. The chordal core 18, illustrated in more detail in FIGS. 2 and 4, has a linear chordal axis 20 that is colinear with a chord 13 extending through the annular forging 12. The chord 13, by definition, is normal to and bisected by a radius R of the annular forging 12. The method further includes forming or machining the test specimen 10 from the chordal core 18. The test specimen is symmetrical about the chordal axis 20.

Figure 3:
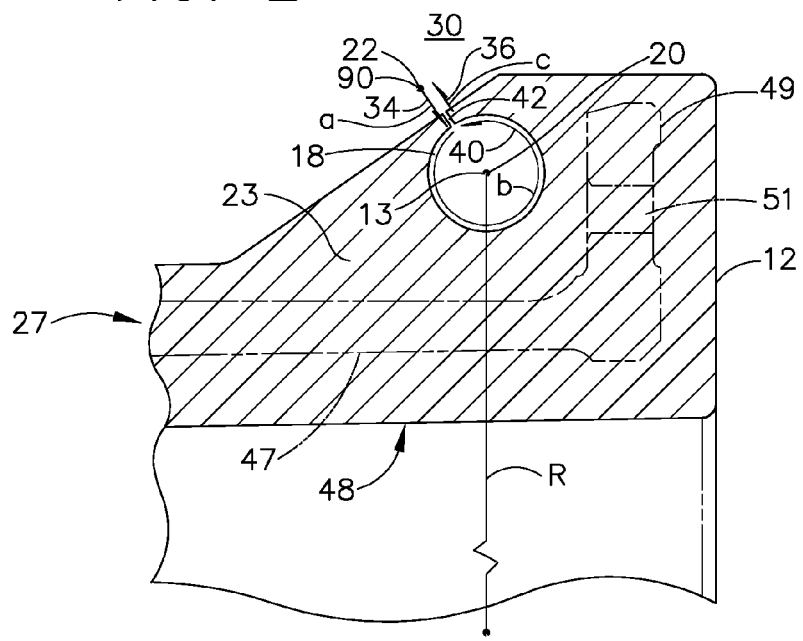
FIG. 3 is a circumferential cross sectional view illustration of the chordal core in the fat of the forging illustrated in FIG. 2.

Referring to FIG. 5, the test specimen 10 illustrated herein includes a gauge section 38 disposed between threaded grips 44. The gage section 38 has a gauge length L and gauge diameter D. Fillets 46 transition the gauge section 38 to the threaded grips 44. The chordal core 18 is machined out from fat 23 of the forging and modern day forgings are usually near net shape 48 having small fats 23 as illustrated in FIG. 3. The final part shape illustrated as an annular casing 47 with flange 49 having bolt holes 51 disposed therethrough is formed by machining the forging 12 including machining away the fat 23. The gauge diameter D is in a range of 0.1-0.5 inches. This is particularly useful because very often the fat has a very small cross-sectional area. This also allows for the use of machine heads with relatively small travel, e.g. 4 inches in X and Y directions.

The machining 30 out of the chordal core 18 may performed using electrical discharge machining (EDM) or another method using a linear cutting tool 22. Linear EDM employs a tool such as an EDM wire 90 of an EDM machine 100 illustrated in FIGS. 9-13. Other types of EDM tools contemplated by the method disclosed herein includes copper tubes and circular wires.

The exemplary embodiment of the annular forging 12 illustrated herein is a single piece integrally formed near net shape annular forging 12 as partially illustrated in cross section in FIG. 3. The near net shape forging 12 includes fat 23 which is machined away during final shape machining to produce the annular part 27 outline in dashed line which is illustrated as the casing described above. The chordal core 18 is machined out of the fat 23 in the exemplary embodiment of the machining 30 illustrated herein. The machining 30 in FIG. 3 generally includes a linear plunge inward a, a circular plunge b around the chordal axis 20, and a linear plunge outward c.

Figure 6:
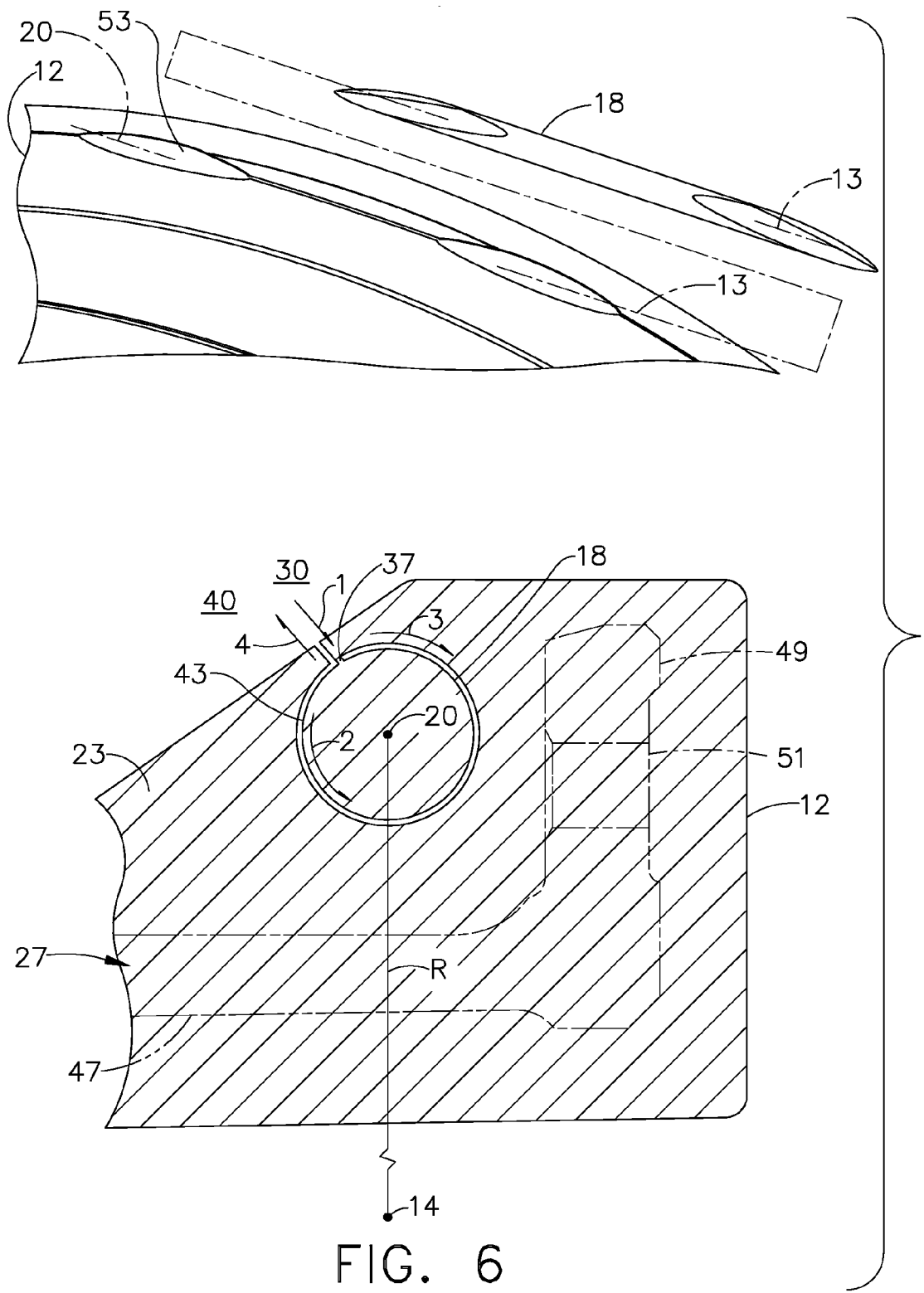
FIG. 6 is a diagrammatic view illustration of a first method of electrical discharge machining out a cylindrical chordal core illustrated in FIG. 4.
Figure 7:
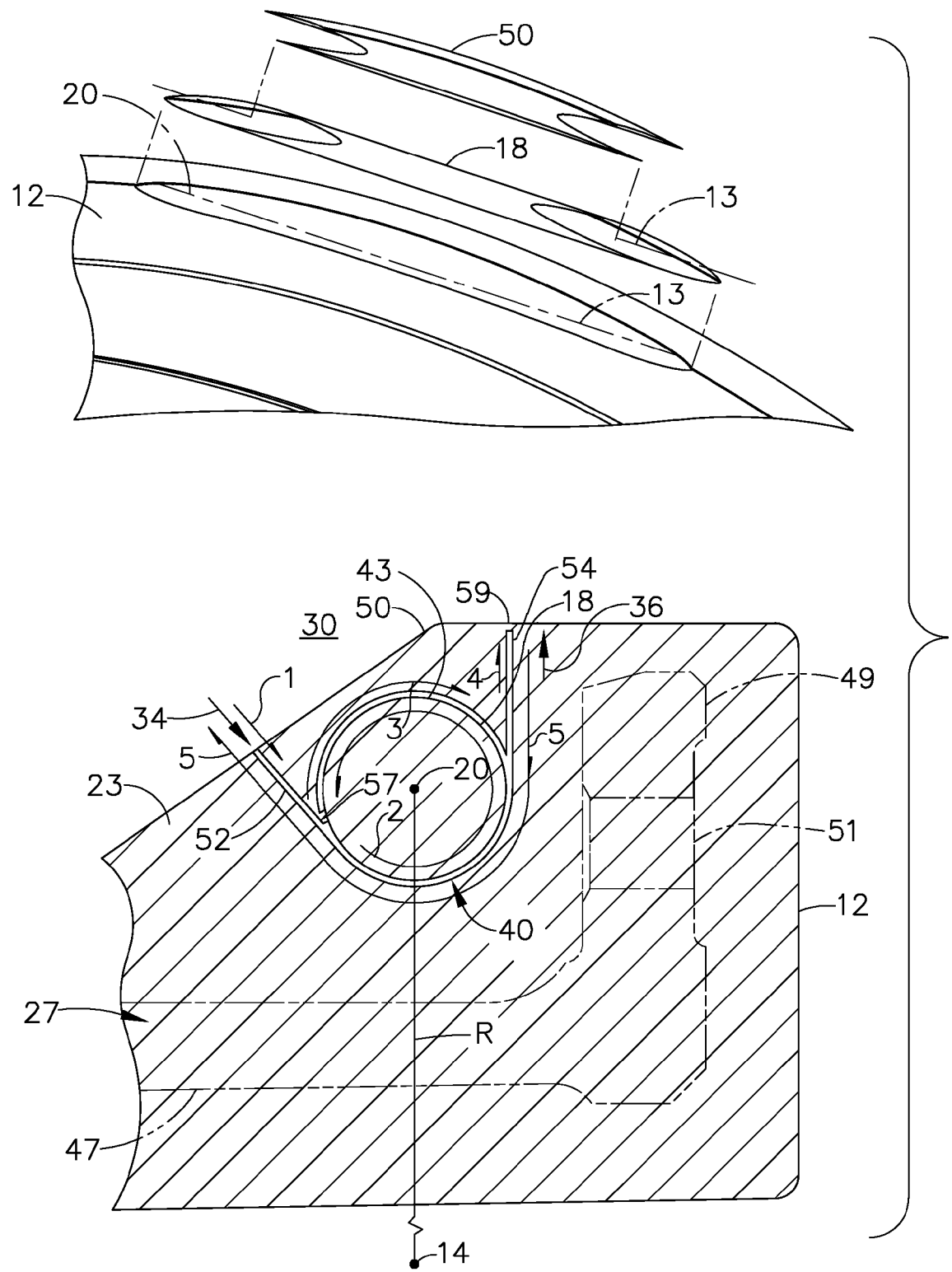
FIG. 7 is a diagrammatic view illustration of a second method of electrical discharge machining a cylindrical chordal core.
Figure 8:
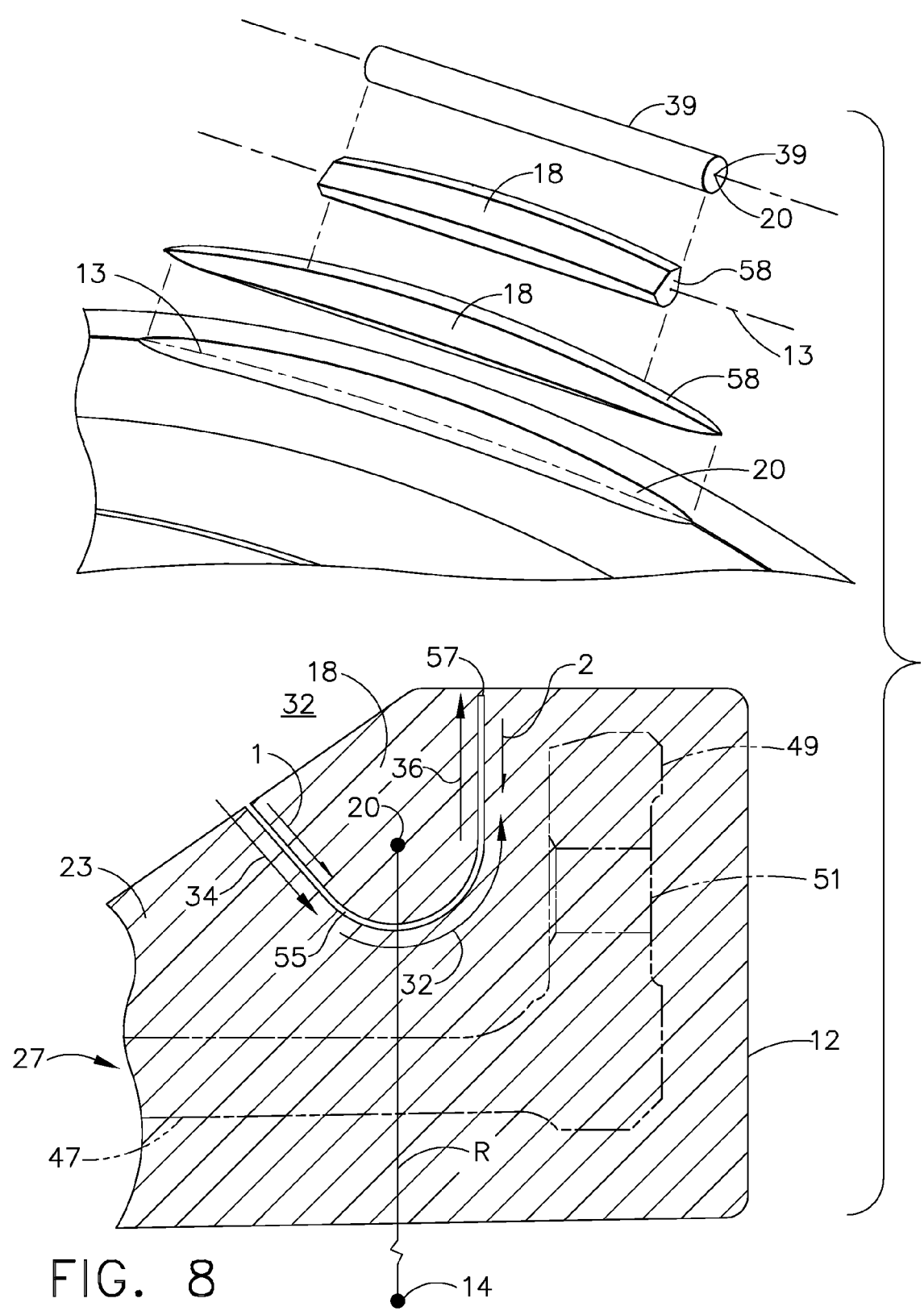
FIG. 8 is a diagrammatic view illustration of a third method of electrical discharge machining a non cylindrical chordal core and machining it to a cylindrical shape.
Figure 9:
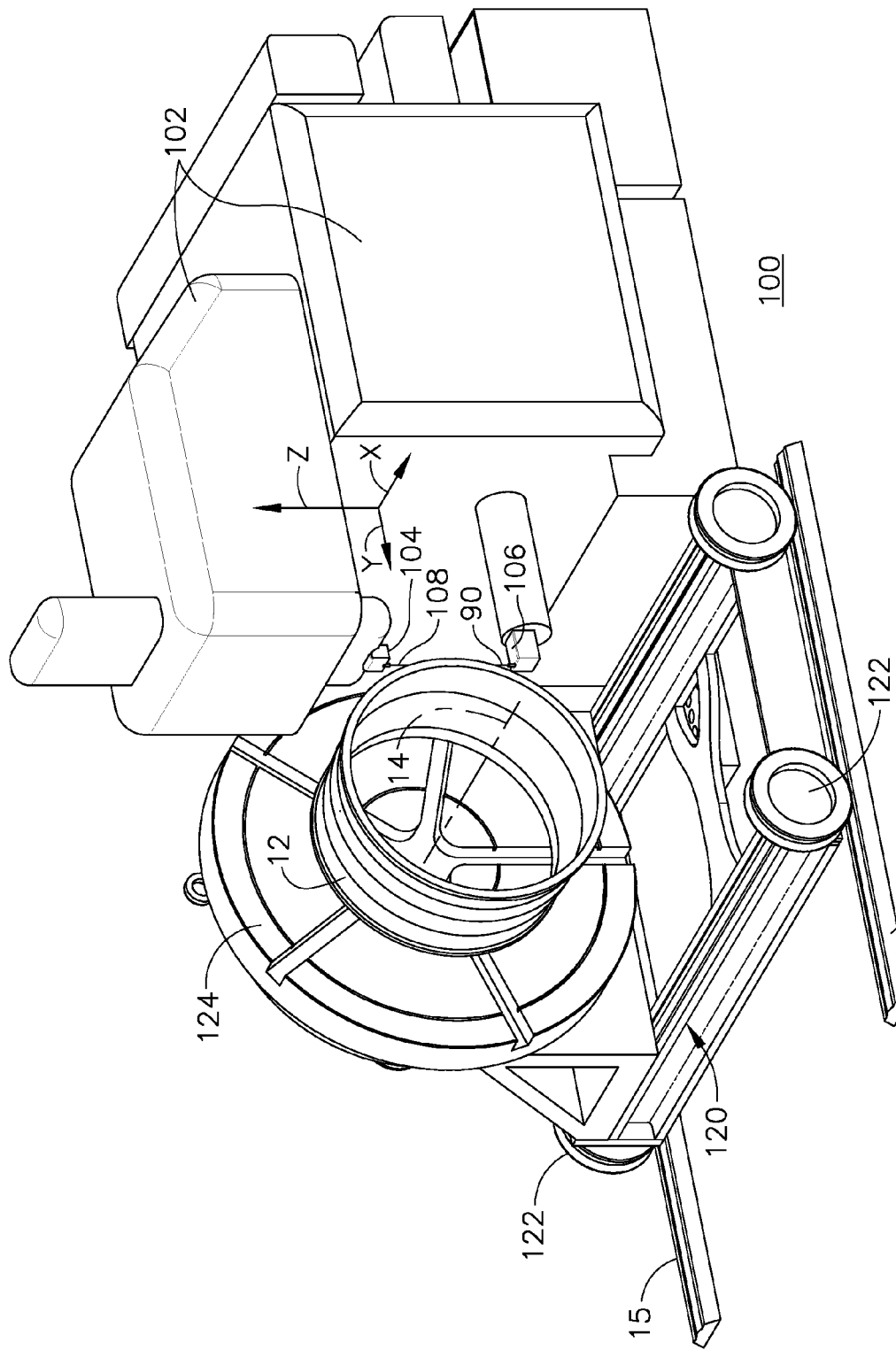
FIG. 9 is a perspective view illustration of an exemplary EDM machine for machining chordal cores.
Figure 10:
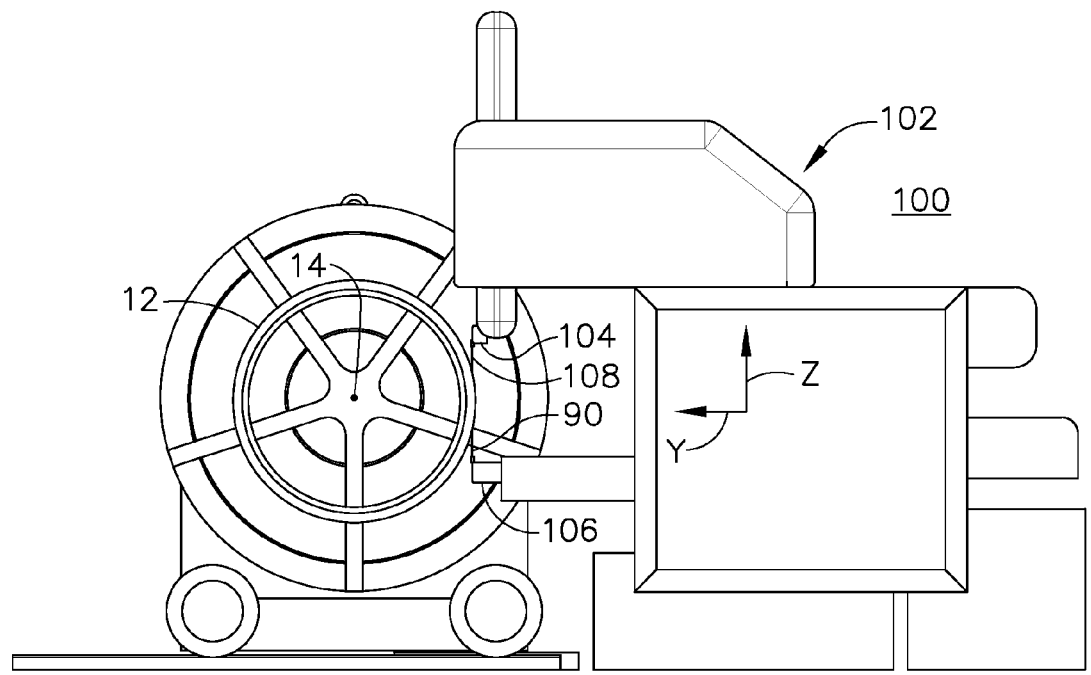
FIG. 10 is a side view illustration of the EDM machine illustrated in FIG. 9.
Figure 11:
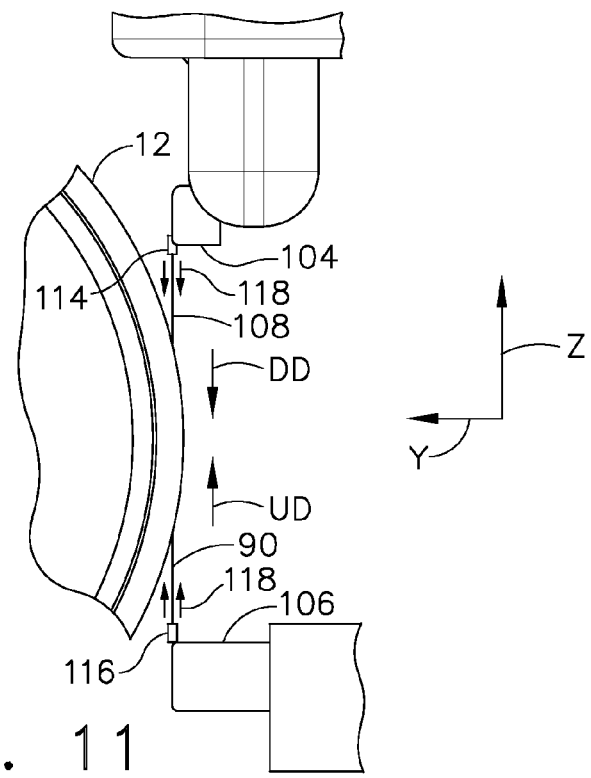
FIG. 11 is an enlarged side view illustration of an EDM wire of the EDM machine illustrated in FIG. 10.
Figure 12:
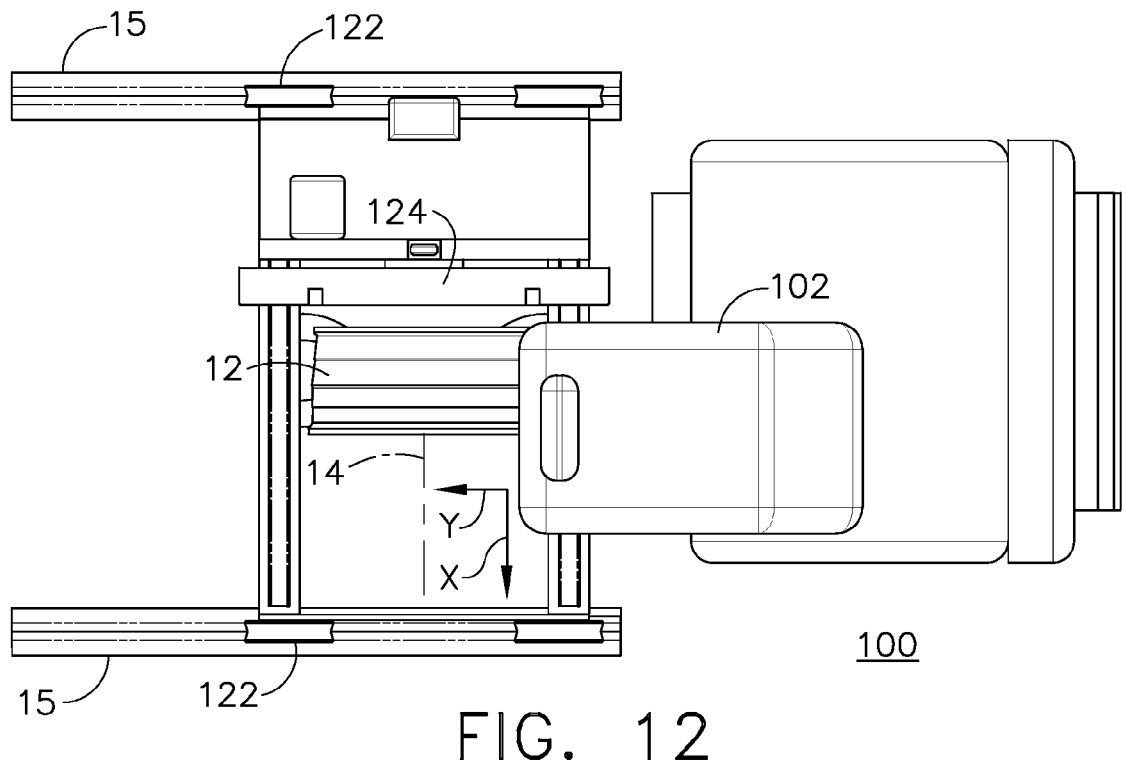
FIG. 12 is a top view illustration of the EDM machine illustrated in FIG. 9.
Figure 13:
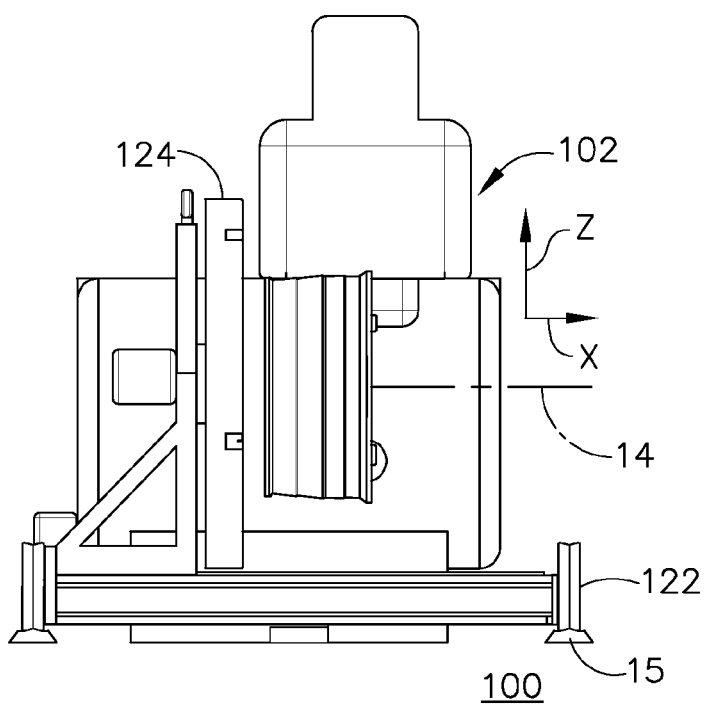
FIG. 13 is a front view illustration of the EDM machine illustrated in FIG. 9.

The machining 30 as illustrated herein includes at least a partially cylindrical cutting 32 about the chordal axis 20 with the linear cutting tool 22 or, more particularly, by a wire EDM process using an EDM wire 90. A partially cylindrical cutting 32 is illustrated in FIG. 8. Substantially full cylindrical cuttings 40 about the chordal axis 20 are illustrated in FIGS. 3, 6, and 7. A full cylindrical cutting 40 embodiment of the machining 30 is generally illustrated in FIG. 3 and includes in sequence, a first linear plunge 34 into the forging 12, the substantially full cylindrical cutting 40 about the chordal axis 20, and a second linear plunge 36 out of the forging 12 through a kerf 42 formed by the first linear plunge 34.

Illustrated in FIG. 6 is the use of one or more supports or bridges 37 between the chordal core 18 and the rest of the forging 12 are left in place to support the chordal core 18 while it is being is machined out. In a more particular embodiment, the machining 30 including the full cylindrical cutting 40 sequentially includes a radially inward linear cutting 1 towards the chordal axis 20, a counter-clockwise annular cutting 2 about the chordal axis 20 stopping at the bridge 37, a clockwise annular cutting 3 about the chordal axis 20 through an annular kerf 43 formed by the counter-clockwise annular cutting 2, and a radially outward linear cutting 4 away from the chordal axis 20. The clockwise and counter-clockwise cuttings may be reversed in sequence such that the clockwise annular cutting is performed before the counter-clockwise cutting. The chordal core 18 is removed tangentially with respect to the forging axis of revolution 14 and is slid out through a cylindrical hole 53 defined by the annular kerf 43.

Another full cylindrical cutting 40 embodiment of the machining 30, illustrated in FIG. 7, includes in sequence, a first linear plunge 34 into the forging 12, the substantially full cylindrical cutting 40 about the chordal axis 20, and a second linear plunge 36 out of the forging 12 wherein the first and second linear plunges are angularly spaced apart with respect to the chordal axis 20. The first and second linear plunges 34, 36 and the substantially full cylindrical cuttings 40 are sufficiently deep that a cap 50 is formed outside of an annular kerf 43 formed by the substantially full cylindrical cutting 40 and between first and second linear kerfs 52, 54 formed by the first and second linear plunges 34, 36. The cap 50 is removed and then the chordal core 18 is removed radially or tangentially with respect to the forging axis of revolution 14.

In a more particular embodiment, the machining 30 sequentially includes an inward linear cutting 1 into the fat 23 of forging 12, a counter-clockwise annular cutting 2 about the chordal axis 20 stopping at a bridge 57, a clockwise annular cutting 3 about the chordal axis 20 through an first annular kerf 60 formed by the counter-clockwise annular cutting 2, an outward linear cutting 4 out of the fat 23 of forging 12 stopping at a second bridge 59. Then, in sequence, cutting or traversing 5 by the linear tool through a second linear kerf 54 formed by the outward linear cutting 4, the first annular kerf 60, and the first linear kerf 52 formed by the inward linear cutting 1. The clockwise and counter-clockwise cuttings may be reversed in sequence such that the clockwise annular cutting is performed before the counter-clockwise cutting. The first and second bridges 57, 59 are machined away or otherwise removed and then the cap 50 and the chordal core 18 are removed.

The partially cylindrical cutting 32 embodiment of the machining 30, illustrated in FIG. 8 includes in sequence, a first linear plunge 34 into the forging 12, the partially cylindrical cutting 32 about the chordal axis 20, and a second linear plunge 36 in a direction out of the forging 12 wherein the first and second linear plunges 34, 36 are angularly spaced apart with respect to the chordal axis 20. The second linear plunge 36 stops at a bridge 57 and the tool or EDM wire retraces its path through a kerf 55 formed by the first linear plunge 34, the partially cylindrical cutting 32, and the second linear plunge 36. The bridge 57 is left in place to support the chordal core 18 while it is being machined out. The chordal core 18 has a partially cylindrical shape 58 and is machined to a cylindrical shape 39 with the chordal axis 20 substantially being an axis of revolution of the cylindrical shape 39.

Illustrated in FIGS. 9-13 is an exemplary embodiment of an EDM machine 100 suitable for machining 30 out a chordal core 18 from an annular forging 12 for making a test specimen 10. The EDM machine 100 illustrated herein includes machining head 102 supporting upper and lower wire guides 104, 106 which guide a cutting portion 180 of the EDM wire 90 extending between the upper and lower wire guides 104, 106. The upper and lower wire guides 104, 106 include upper and lower nozzles 114, 116 operable for directing jets 118 of machining fluid or dielectric in opposing coaxial down and up directions DD, UD respectively along the cutting portion 180 of the EDM wire 90 as more particularly illustrated in FIG. 11. The machining head 102 is operable to move at least in perpendicular X and Y directions. The headstock 102 is moved in a Z direction as close to the annular forging 20 as possible. Thus, the jets 118 of machining fluid or dielectric are directed in up and down Z directions along the cutting portion 180 of the EDM wire 90 which is parallel to the Z direction.

A carrier 120 for holding the annular forging 12 incudes wheels 122 which engage and ride along parallel rails 15 and a headstock 124 operable for mounting and securing the annular forging 12 to the carrier 120. The headstock 124 is positioned on the carrier 120 for holding the annular forging 12 such that the forging axis 14 is parallel to the X direction. The forging 12 is mounted to the carrier 120 and oriented to allow the carrier to present the forging 12 to the machining head 102 such that the cutting portion 180 of the EDM wire 90 is tangential to the annular forging 12. The machining head 102 is operable to effect movement in X and Y directions to provide linear and circular cutting or machining in the X and Y directions and have limited travel with respect to the forging 12 in the X and Y directions. The carrier 120 is operable to translate in the Y direction in order to present the forging 12 to the machining head 102. Either or both the carrier 120 and the machining head 102 can effect positioning of the forging 12 with respect to the machining head 102 in a Z direction. The X, Y, and Z directions all being orthogonal. All movements of the carrier 120 and the machining head 102 during the machining or cutting operation are controlled by a CNC controller not illustrated in the FIGS.

Figure 14:
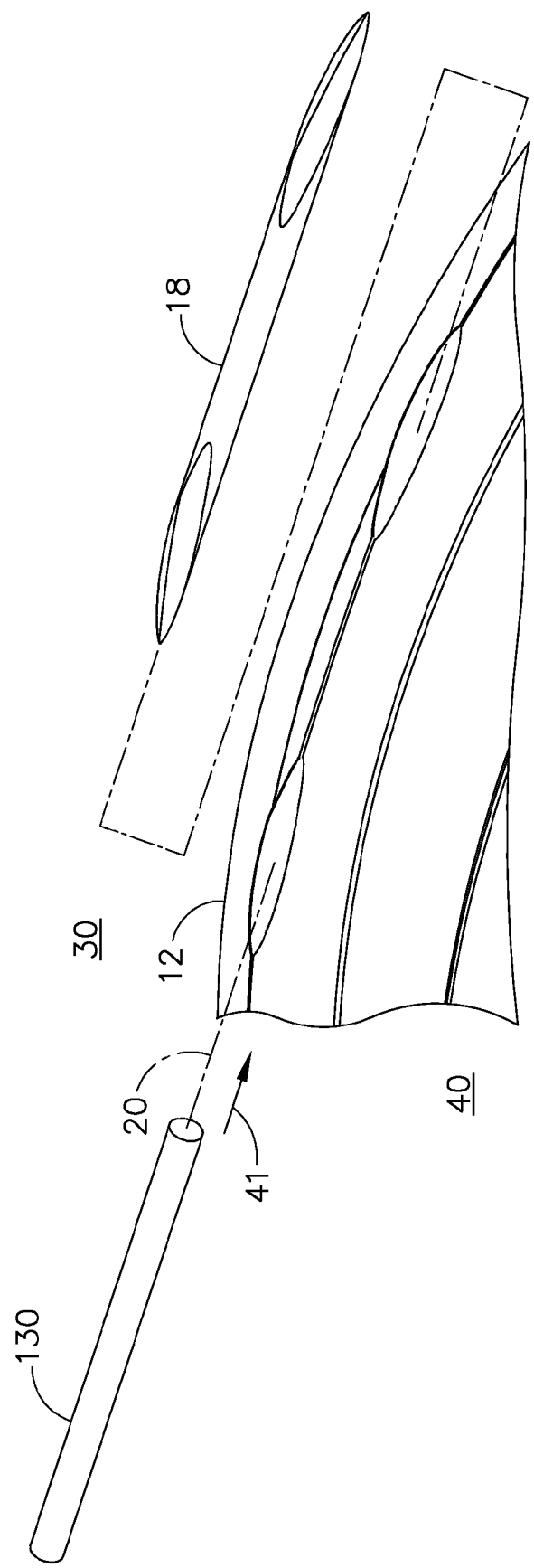
FIG. 14 is a diagrammatic view illustration of a method of electrical discharge machining out a cylindrical chordal core using an annular electrode.

Another full cylindrical cutting 40 embodiment of the machining 30, illustrated in FIG. 14, includes a first tangential plunge 41 with a copper or brass tubular electrode 130, which may be an annular electrode in the form of a copper or brass tube, through the forging 12 to machine out the chordal core 18. Other types of EDM tools or annular electrodes contemplated by the methods disclosed herein include circular wires.

Figure 15:
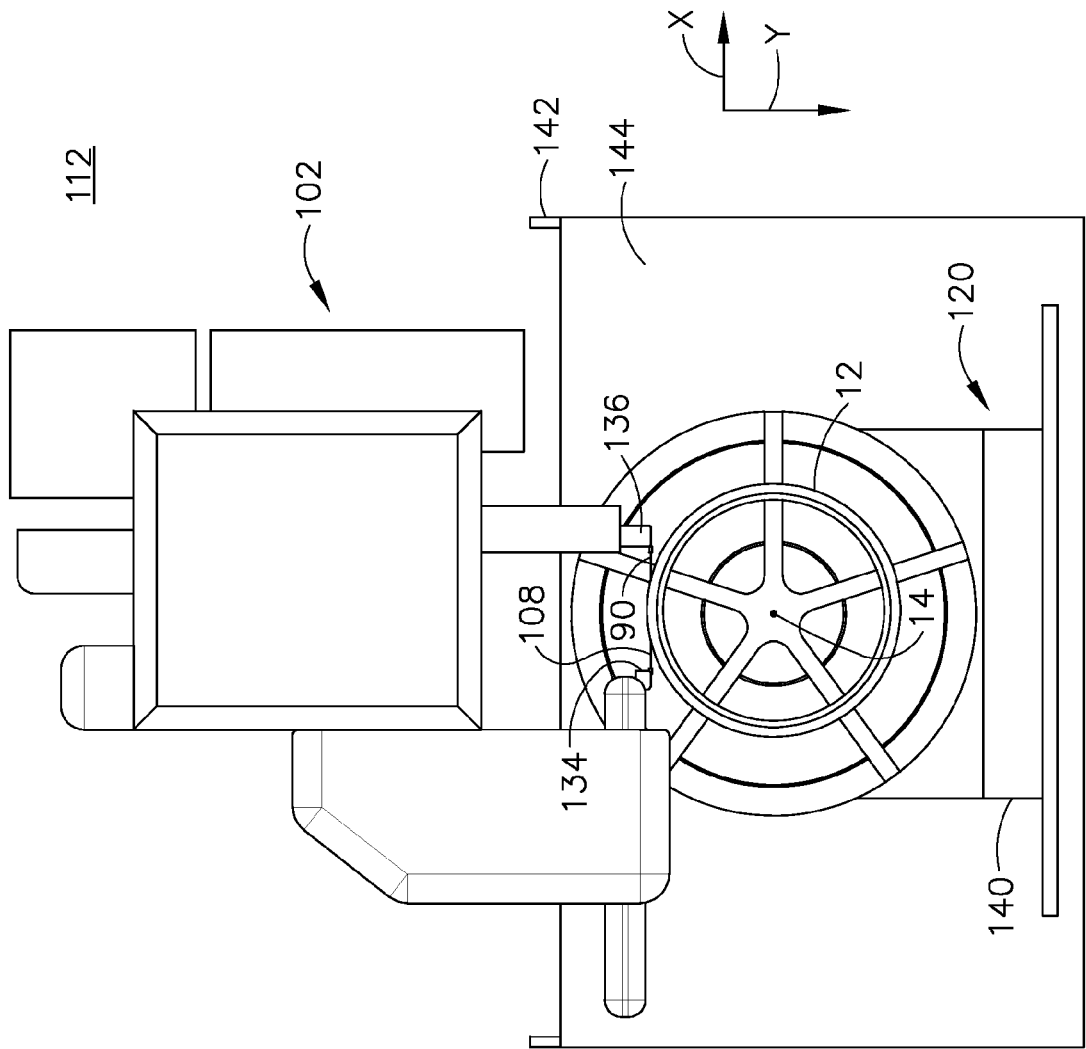
FIG. 15 is a side view illustration of another exemplary EDM machine for machining chordal cores of a forging submerged in a tank of dielectric.

Illustrated in FIG. 15 is another EDM machine 112 suitable for machining 30 out the chordal core 18 from an annular forging 12 for making the test specimen 10. The carrier 120 is a movable table 140 in a tank 142 filled with the machining fluid or dielectric 144. The annular forging 12 is submerged in the machining fluid or dielectric during the EDM process. The EDM machine 112 illustrated herein includes the machining head 102 supporting first and second wire guides 134, 136 which guide a cutting portion 180 of the EDM wire 90 extending between the first and second wire guides 134, 136. Because the portion of the forging 12 that is being EDMed is submerged, there is no need for nozzles operable for directing jets of machining fluid or dielectric in opposing directions coaxial up and down along the cutting portion 180 of the EDM wire 90. The machining head 102 is illustrated as being operable to move at least in perpendicular X and Y directions that are normal to up and down directions. The machining head 102 can be oriented at some other angle, i.e. at 90 degrees such that the head moves in perpendicular X and Y directions for and one of the X and Y directions is parallel to the up and down directions.

The headstock 124 is mounted to the table 140. The headstock 124 is positioned on the table 140 for holding the annular forging 12 such that the forging axis is parallel to the X or Y direction depending on the orientation of the machining head 102. The forging 12 is mounted to the carrier 120 and oriented to allow the carrier to present the forging 12 to the machining head 102 such that the cutting portion 180 of the EDM wire 90 is tangential to the annular forging 12. The machining head 102 is operable to effect movement in X and Y directions to provide linear and circular cutting or machining in the X and Y directions and have limited travel with respect to the forging 12 in the X and Y directions. The table 140 is operable to translate in the Y direction in order to present the forging 12 to the machining head 102. Either or both the table 140 and the machining head 102 can effect positioning of the forging 12 with respect to the machining head 102 in a Z direction. The X, Y, and Z directions all being orthogonal. All movements of the table 140 and the machining head 102 during the machining or cutting operation are controlled by a CNC controller not illustrated in the FIGS.

While there have been described herein what are considered to be preferred embodiments of the present invention, other modifications of the invention shall be apparent to those skilled in the art from the teachings herein, and it is, therefore, desired to be secured in the appended claims all such modifications as fall within the true spirit and scope of the invention.

While the preferred embodiment of our invention has been described fully in order to explain its principles, it is understood that various modifications or alterations may be made to the preferred embodiment without departing from the scope of the invention as set forth in the appended claims.

What is claimed is:

1. A method for making a test specimen from an annular forging having a forging axis of revolution, the method comprising:
   machining out a chordal core from the forging,
   the chordal core having a linear chordal axis colinear with a chord extending through the annular forging, and
   forming the test specimen from the chordal core, the test specimen being symmetrical about the chordal axis.

2. A method as claimed in claim 1, further comprising using a linear cutting tool for the machining.

3. A method as claimed in claim 2, further comprising the machining including at least a partially cylindrical cutting about the chordal axis with the linear cutting tool.

4. A method as claimed in claim 3, further comprising:
   the machining including in sequence,
   a first linear plunge into the forging,
   the partially cylindrical cutting, and
   a second linear plunge out of the forging wherein the first and second linear plunges are angularly spaced apart with respect to the chordal axis.

5. A method as claimed in claim 2, further comprising the machining including a substantially full cylindrical cutting about the chordal axis.

6. A method as claimed in claim 5, further comprising:
   the machining including in sequence,
   a first linear plunge into the forging,
   the substantially full cylindrical cutting, and a second linear plunge out of the forging through a kerf formed by the first linear plunge.

7. A method as claimed in claim 5, further comprising:
the machining including in sequence,
a first linear plunge into the forging,
the substantially full cylindrical cutting, and
a second linear plunge out of the forging wherein the first and second linear plunges are angularly spaced apart with respect to the chordal axis.

8. A method as claimed in claim 2, further comprising the machining including electrical discharge machining and the linear cutting tool being a wire electrical discharge machining machine.

9. A method as claimed in claim 8, further comprising the machining including at least a partially cylindrical cutting about the chordal axis with the linear cutting tool.

10. A method as claimed in claim 9, further comprising:
the machining including in sequence,
a first linear plunge into the forging,
the partially cylindrical cutting, and
a second linear plunge out of the forging wherein the first and second linear plunges are angularly spaced apart with respect to the chordal axis.

11. A method as claimed in claim 8, further comprising the machining including a substantially full cylindrical cutting about the chordal axis.

12. A method as claimed in claim 11, further comprising:
the machining including in sequence,
a first linear plunge into the forging,
the substantially full cylindrical cutting, and
a second linear plunge out of the forging through a kerf formed by the first linear plunge.

13. A method as claimed in claim 11, further comprising:
the machining including in sequence,
a first linear plunge into the forging,
the substantially full cylindrical cutting, and
a second linear plunge out of the forging wherein the first and second linear plunges are angularly spaced apart with respect to the chordal axis.

14. A method as claimed in claim 1, further comprising the machining including electrical discharge machining using a tubular electrode for the machining.

15. A method as claimed in claim 14 further comprising the tubular electrode being a copper or brass tubular electrode.

16. A method as claimed in claim 1, further comprising the chordal core being fully machined from fat of the forging.

17. A method as claimed in claim 16, further comprising using a linear cutting tool for the machining.

18. A method as claimed in claim 17, further comprising the machining including at least a partially cylindrical cutting about the chordal axis with the linear cutting tool.

19. A method as claimed in claim 18, further comprising:
the machining including in sequence,
a first linear plunge into the forging,
the partially cylindrical cutting, and
a second linear plunge out of the forging wherein the first and second linear plunges are angularly spaced apart with respect to the chordal axis.

20. A method as claimed in claim 17, further comprising the machining including a substantially full cylindrical cutting about the chordal axis.

21. A method as claimed in claim 20, further comprising:
the machining including in sequence,
a first linear plunge into the forging,
the substantially full cylindrical cutting, and
a second linear plunge out of the forging through a kerf formed by the first linear plunge.

22. A method as claimed in claim 20, further comprising:
the machining including in sequence,
a first linear plunge into the forging,
the substantially full cylindrical cutting, and
a second linear plunge out of the forging wherein the first and second linear plunges are angularly spaced apart with respect to the chordal axis.

23. A method as claimed in claim 17, further comprising the machining including electrical discharge machining and the linear cutting tool being a wire electrical discharge machining machine.

24. A method as claimed in claim 23, further comprising the machining including at least a partially cylindrical cutting about the chordal axis with the linear cutting tool.

25. A method as claimed in claim 24, further comprising:
the machining including in sequence,
a first linear plunge into the forging,
the partially cylindrical cutting, and
a second linear plunge out of the forging wherein the first and second linear plunges are angularly spaced apart with respect to the chordal axis.

26. A method as claimed in claim 23, further comprising the machining including a substantially full cylindrical cutting about the chordal axis.

27. A method as claimed in claim 26, further comprising:
the machining including in sequence,
a first linear plunge into the forging,
the substantially full cylindrical cutting, and
a second linear plunge out of the forging through a kerf formed by the first linear plunge.

28. A method as claimed in claim 26, further comprising:
the machining including in sequence,
a first linear plunge into the forging,
the substantially full cylindrical cutting, and
a second linear plunge out of the forging wherein the first and second linear plunges are angularly spaced apart with respect to the chordal axis.

29. A method as claimed in claim 16, further comprising the machining including electrical discharge machining using a tubular electrode for the machining.

30. A method as claimed in claim 29 further comprising the tubular electrode being a copper or brass tubular electrode.

31. A method as claimed in claim 2, further comprising forming the test specimen with a gauge section diameter in a range of 0.1-0.5 inches.

32. A method as claimed in claim 31, further comprising the machining including electrical discharge machining and the linear cutting tool being a wire electrical discharge machining machine.

33. An electrical discharge machining method for making a test specimen from an annular forging having a forging axis of revolution, the method comprising:
mounting the annular forging in a headstock of carrier of an electrical discharge machining machine,
the electrical discharge machining machine having a machine head operable for moving and machining in perpendicular X and Y directions and the carrier being operable to translate in the Y direction perpendicular to a forging axis of revolution of the forging,
presenting the forging to the machine head by translating the carrier in the Y direction,
machining out a chordal core from the forging electrical discharge machining using the machine head moving in the X and Y directions,
the chordal core having a linear chordal axis colinear with a chord extending through the annular forging, and forming the test specimen from the chordal core, the test specimen being symmetrical about the chordal axis.

34. A method as claimed in claim 33, further comprising directing jets of machining fluid or dielectric in up and down Z directions perpendicular to both the X and Y directions and along a cutting portion of an electrical discharge machining wire which is parallel to the Z directions.

35. A method as claimed in claim 34, further comprising directing the jets from upper and lower nozzles of upper and lower wire guides respectively supported by the machining head wherein the cutting portion of the electrical discharge machining wire extends between the upper and lower wire guides.

36. A method as claimed in claim 33, further comprising the carrier being a movable table in a tank of the machining fluid or dielectric and the annular forging being submerged in the machining fluid or dielectric.

37. A method as claimed in claim 33, further comprising forming the test specimen with a gauge section diameter in a range of 0.1-0.5 inches.

38. A method as claimed in claim 37, further comprising the machining including electrical discharge machining and the linear cutting tool being a wire electrical discharge machining machine.

\* \* \* \* \*